(12) United States Patent
Grenet

(10) Patent No.: US 9,958,470 B2
(45) Date of Patent: May 1, 2018

(54) SYSTEM FOR CAPTURING MOVEMENTS OF AN ARTICULATED STRUCTURE

(71) Applicants: MOVEA, Grenoble (FR); COMMISSARIAT A L'ENERGIE ATOMIQUE ET AUX ENERGIES ALTERNATIVES, Paris (FR)

(72) Inventor: Pierre Grenet, Grenoble (FR)

(73) Assignees: Movea, Grenoble (FR); Commissariat A L'energie Atomique et Aux Energies Alternatives, Paris (FR)

( * ) Notice: Subject to any disclaimer, the term of this patent is extended or adjusted under 35 U.S.C. 154(b) by 733 days.

(21) Appl. No.: 14/382,998

(22) PCT Filed: Mar. 7, 2013

(86) PCT No.: PCT/EP2013/054561
§ 371 (c)(1),
(2) Date: Sep. 4, 2014

(87) PCT Pub. No.: WO2013/131989
PCT Pub. Date: Sep. 12, 2013

(65) Prior Publication Data
US 2015/0032408 A1     Jan. 29, 2015

(30) Foreign Application Priority Data
Mar. 8, 2012   (FR) .................................. 12 52103

(51) Int. Cl.
| | | |
|---|---|---|
| *G06F 19/00* | (2011.01) | |
| *G01P 15/00* | (2006.01) | |
| *G06F 3/01* | (2006.01) | |
| *A61B 5/11* | (2006.01) | |
| *A63B 71/06* | (2006.01) | |

(52) U.S. Cl.
CPC ............ *G01P 15/00* (2013.01); *A61B 5/1116* (2013.01); *A63B 71/06* (2013.01); *G06F 3/011* (2013.01)

(58) Field of Classification Search
CPC ........ H01G 11/38; H01G 11/86; H01G 9/058; Y02E 60/13
USPC ................................ 702/141, 150, 182–185
See application file for complete search history.

(56) References Cited

U.S. PATENT DOCUMENTS 6,997,882 B1 * 2/2006 Parker .......................... 600/301
2004/0051680 A1   3/2004 Azuma et al.

OTHER PUBLICATIONS

International Search Report and Written Opinion from PCT/EP2013/054561, mailed on Jun. 20, 2013.

(Continued)

*Primary Examiner* — Edward Raymond
(74) *Attorney, Agent, or Firm* — Stroock & Stroock & Lavan LLP

(57) ABSTRACT

A system for capturing the movements of a body having substantially rigid segments articulated together includes attitude units fastened onto the segments of the body, the units each including at least one accelerometer and one magnetometer, and a reduced number of gyroscopes. The system also includes a pseudo-static state detection module and a module for calculating pseudo-static angles. When all segments are detected in a pseudo-static state, the state vector is provided by the module for calculating pseudo-static angles. When a segment is detected in a dynamic state, the state vector is provided at the output of a Kalman filter.

18 Claims, 3 Drawing Sheets

(56) References Cited

OTHER PUBLICATIONS

Kalman filter—Wikipedia, Mar. 2012.
Welch et al., "An introduction to the Kalman filter", Computer Graphics,Conference Proceedings, Los Angeles, CA, Aug. 12-17, 2001.
Luinge H., "Inertial Sensing of Human Movements ", Thesis University of Twente, Twene University Press, 2002, pp. 1-88.
Sabatini, "Estimating Three-Dimensional Orientation of Human Body Parts by Inertial/Magnetic Sensing", Sensors, 11(2): pp. 1489-1525, Jan. 26, 2011.
Saxena et al., "In USe Parameter Estimation of Inertial Sensors by Detecting Multilevel Quasi-static States" Field Programmable Logic and Applicaxtion, Sep. 14, 2005. vol. 3684, pp. 595-601.
Azuma et al., "Improving Static and Dynamic Registration in an Optical See-Through HMD", SIGGRAPH Conference Proceedings, Jul. 24, 1994, pp. 197-204.

\* cited by examiner

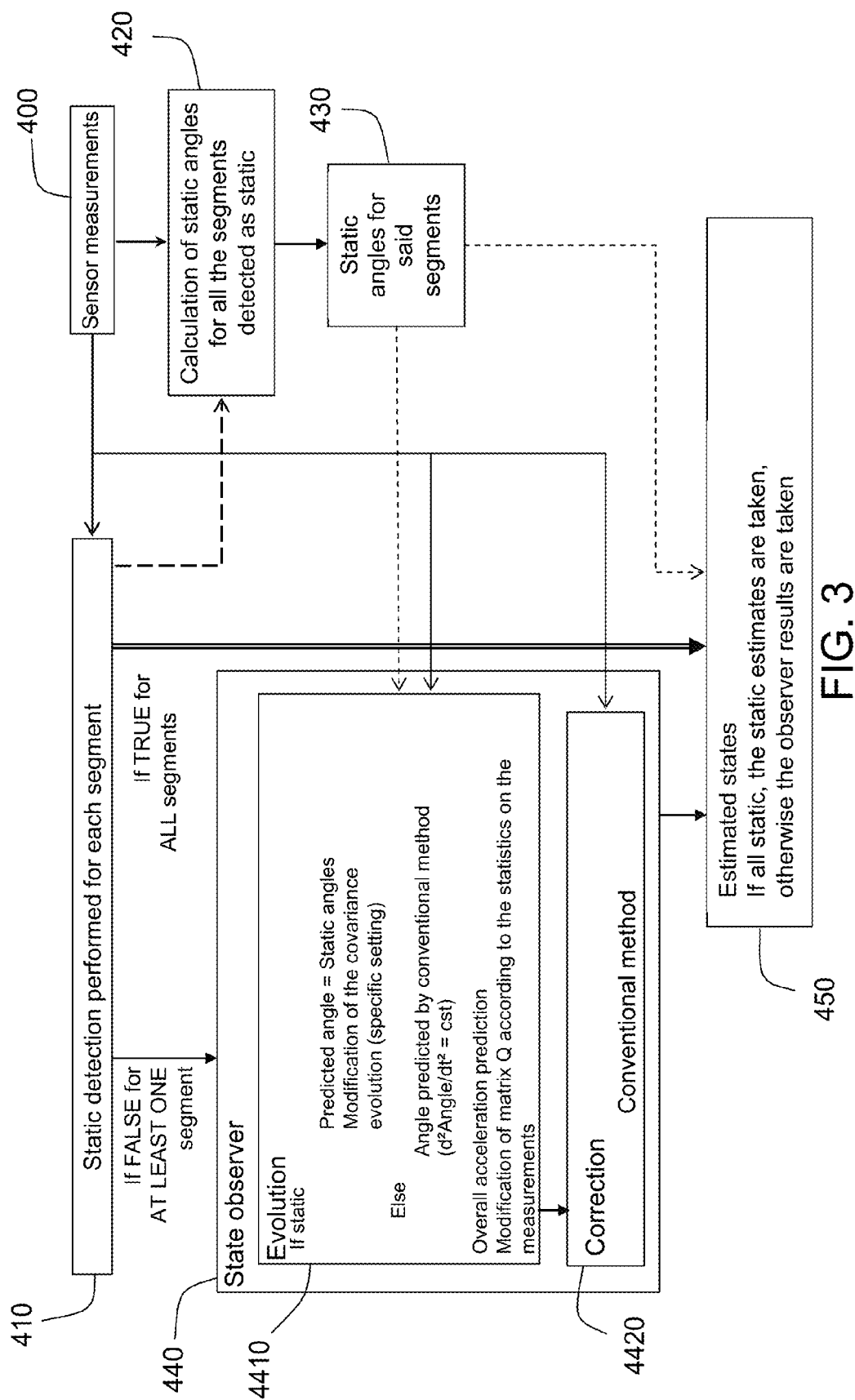

SYSTEM FOR CAPTURING MOVEMENTS OF AN ARTICULATED STRUCTURE

CROSS-REFERENCE TO RELATED APPLICATIONS

This application is the National Stage of International Application No. PCT/EP2013/054561, filed Mar. 7, 2013, which claims foreign priority to French Application No. 1252103, filed Mar. 8, 2012, the contents of both of which are incorporated herein by reference.

BACKGROUND

1. Field of the Invention

The present invention relates to a method of resolution using a measurement system arranged on an articulated or non-articulated structure with a view to capturing the movements thereof. In the event that this structure is a person or an animal, it can be applied, for example, to the fields of medicine, movie animation, sports or video games.

2. Description of the Related Art

Since its first fields of application, which are medicine and movie animation, the capture of the movement of a whole human body is a technique that is rapidly expanding, which has seen its use become widespread, notably in sport and video games. Indeed, the democratization of microelectromechanical systems, better known under the English acronym MEMS, notably the democratization of inertial and magnetic sensors such as accelerometers, magnetometers and gyroscopes, has enabled the spread of very compact devices called 'attitude units' which are capable of assessing their own orientation with respect to a terrestrial reference frame. There are various types of attitude units according to the sensors that they combine. However, in the prior art, only the combination of an accelerometer with a magnetometer and a gyroscope in an attitude unit can be used for estimating the kinematic orientation of said unit satisfactorily in the presence of unknown acceleration, i.e. without any a priori knowledge about its movement or in the presence of magnetostatic interference. Indeed, the orientation of the unit with a non-zero proper acceleration of said unit can only be estimated in the case of a data fusion with three modalities called AGM (Accelerometers, Magnetometers and Gyroscopes) fusion. In the case of a fusion with two modalities called AM (Accelerometers and Magnetometers) fusion, kinematic orientation cannot be estimated, since the acceleration and gravitation information contained in the accelerometer measurement are inseparable.

Thus, a solution for capturing kinematic movement of the whole body called Moven has been developed by the company Xsens. This solution is described in a document entitled *Inertial Sensing Of Human Movement* (H. J. Luinge). It is based on attitude units known under the trade name MTx. Each MTx combines a triaxial accelerometer with a triaxial magnetometer and a triaxial gyroscope, thus providing the orientation and displacement of the segment of the body on which it is fixed, whether this is the shoulder, the arm or the forearm, for example. Then the segments are associated in keeping with the skeleton. Seventeen MTxs are thus judiciously distributed in a combination in order to ensure their position on the body. The MTxs are connected by wired connections to two electronic packages responsible for collecting and synchronizing the data from the MTxs. The Xbus Masters communicate with a computer through a wired or wireless connection. Unfortunately, attitude units such as the MTxs, which combine an accelerometer with a magnetometer and a gyroscope, have a fairly high energy consumption. MTxs are especially expensive, which may not be economically justified in some fields. These are drawbacks that the present invention intends to address.

The French patent application FR 2 916 069 A1 describes another solution for capturing the kinematic movements of the whole body from a toolbox called HuMAnS according to the English acronym for *Humanoid Motion Analysis and Simulation*. This is a set of tools in the C language and Scilab developed by one of the applicants in collaboration with INRIA. Unlike the Moven solution cited previously, which is linked to MTx units, the HuMAnS solution is only software and is not linked to any type of sensors or unit. It can be used, inter alia, for the analysis, modeling and monitoring of humanoid and human movement from a geometric model of the human body for constructing sensor measurements distributed over segments of the body. The HuMAnS solution implements a very simple Kalman filter, which diverges in the case of an AM fusion without gyroscope and only operates satisfactorily by using complete AGM units with 9 axes on each segment. In addition, said patent application does not disclose a measurement system for minimizing the consumption/performance cost ratio.

SUMMARY OF THE INVENTION

Various embodiments of the present invention provide a measurement system suited to an articulated structure, the movement whereof is to be captured, which meets the aim of minimizing the consumption/performance ratio.

In the context of capturing the movements of a whole human body, one aspect of certain embodiments of the invention is notably to add a prioris in order to limit the number of angular velocity sensors, e.g. gyroscopes, which, in general, are more energy-consuming and more expensive than other inertial or magnetic sensors, notably to reduce the overall cost of production and to increase the autonomy of the system. These a prioris notably include the fact that the sensors are fixed in a known manner and/or geometrically calibrated or on an articulated or non-articulated structure and that, accordingly, their relative movements can only be compositions of rotations; they also include the fact of using the algorithms in static mode when the segments are detected in a pseudo-static state.

For this purpose, embodiments of the invention disclose a system for capturing the movements of a structure including a plurality of N substantially rigid segments articulately connected with said structure, said system including a set of N accelerometers with at least one measurement axis, each of said N accelerometers being substantially rigidly connected to one of said N segments; a set of P second sensors capable of returning one direction of a fixed reference frame, each substantially rigidly connected to a segment; a set of Q third sensors capable of returning a measurement representative of an angular velocity, each substantially solidly connected to a segment; a module for communicating the outputs of the N accelerometers, the P second sensors and the Q third sensors with a computer processing module, said processing module including a state observer, said system further including a module for detecting a pseudo-static state of each of the segments of said structure, a module for calculating the pseudo-static orientation of the segments in a pseudo-static state, a state observer module configured for replacing the outputs of the prediction function of the state observer with the outputs of the pseudo-static orientation calculation module for the segments for which the detection condition at the output of the pseudo-static state detection module is true, wherein the number Q is strictly less than the number N and the number P.

Advantageously, R is equal to the number of branches of the structure whereof the movement is captured, the number Q is less than or equal to R+1.

Advantageously, the second sensors are magnetometers.

Advantageously, the third sensors are gyroscopes.

Advantageously, the state observer is a Kalman filter.

Advantageously, the system modules of the invention are configured by state evolution models of the form:

$$\begin{cases} \text{Measurement} = \text{function}(x) \\ \dot{x} = \text{evolution}(x) \end{cases}$$

where:
  x designates a state vector of the body;
  function designates a characteristic measurement function of the accelerometers, magnetometers and gyroscopes;
  Measurement=[Measurement Accelerometer, Measurement Magnetometer, Measurement Gyroscope] designates a measurement vector provided by the accelerometers, magnetometers and gyroscopes;
  $\dot{x}$ designates the first derivative of x with respect to time;
  evolution designates an evolution function of the body state;

Advantageously, the state vector x is of the form $x=[\theta, \dot{\theta}, \ddot{\theta}, Acc_x, Acc_y, Acc_z]$ where $\theta$, $\dot{\theta}$ and $\ddot{\theta}$ respectively designate an orientation angle of the segments, its first derivative and its second derivative with respect to time, where $Acc_x$, $Acc_y$ and $Acc_z$ designate the components of the frame acceleration Acc of the whole of the body in a terrestrial reference frame (X, Y, Z).

Advantageously, the state evolution model of the Kalman filter uses said pseudo-static angles for the segments detected in a pseudo-static state and the state evolution model of the Kalman filter for the segments detected in a dynamic state.

Advantageously, the state evolution model of the Kalman filter uses an assumption of constancy of accelerations of the articulation angles.

Advantageously, the state vector is estimated from the pseudo-static angles at the output of the module for calculating said pseudo-static angles, if all the segments are detected in a pseudo-static state and is estimated by the Kalman filter, if at least one segment is detected in a dynamic state.

Advantageously, the criterion of pseudo-staticity is fulfilled by a segment when at least one of the values provided by at least one of the elements of the group including an attitude unit or a gyroscope which is rigidly connected thereto provides at least one measurement chosen from the norm of an acceleration vector and an angle between said acceleration vector and a magnetic field vector which is less than a predetermined threshold value.

Advantageously, the state evolution model of the Kalman filter predicts the angle $\theta$, its first derivative $\dot{\theta}$ and its second derivative $\ddot{\theta}$ via the function defined by:

$$\dot{x} = \begin{bmatrix} 0 & 0 & 0 & 0 & 0 & 0 \\ 1 & 0 & 0 & 0 & 0 & 0 \\ 0 & 1 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \end{bmatrix} * \left( x + \begin{bmatrix} 0 \\ 0 \\ v_{\ddot{\theta}} \\ 0 \\ 0 \\ 0 \end{bmatrix} \right) + \begin{bmatrix} v_\theta \\ v_{\dot{\theta}} \\ 0 \\ v_{Acc\_x} \\ v_{Acc\_y} \\ v_{Acc\_z} \end{bmatrix}$$

where $v_\theta$, $v_{\dot{\theta}}$, $v_{\ddot{\theta}}$, $v_{Acc\_x}$, $v_{Acc\_y}$ and $v_{Acc\_z}$ are noise terms on the measurement of $\theta$, $\dot{\theta}$, $\ddot{\theta}$, $Acc_x$, $Acc_y$ and $Acc_z$ respectively.

Advantageously, the state evolution model of the Kalman filter predicts the frame acceleration Acc as the mean of the frame accelerations Acc_overall calculated for each accelerometer from the measurement vector Mes_Acc_actual actually provided by said accelerometer, the frame acceleration Acc_overall being calculated for each accelerometer by:

$$Acc\_overall = -^{Earth}R_{Sensor} * (Mes\_Acc\_actual - Mes\_Acc_{Acc\_overall=0})$$

where $^{Earth}R_{Sensor}$ designates a matrix of rotation of a reference frame associated with said accelerometer toward the terrestrial reference frame and $Mes\_Acc_{Acc\_overall=0}$ designates a theoretical measurement vector calculated by assuming that the overall acceleration is zero.

Advantageously, the accelerometer measurement model of the Kalman filter is given by the equation:

$$Mes\_Acc = {}^{Sensor}R_{Earth} * \left( G0 - \left( \frac{\partial^2\,{}^{Earth}T_{Sensor}}{\partial t^2} + Acc\_overall \right) \right)$$

where Mes_Acc designates a vector of measurements taken by said accelerometer, $^{Earth}R_{sensor}$ designates a matrix of rotation of the reference frame associated with the accelerometer toward the terrestrial reference frame, G0 is the earth's gravitational field measured from an initial position in the reference frame associated with the accelerometer and $^{Earth}R_{sensor}$ is a translation vector from the terrestrial reference frame to the reference frame associated with the accelerometer.

Advantageously, the covariances of measurement and state evolution noise are estimated both a priori and a posteriori.

Advantageously, the covariances of state evolution noise are estimated a priori from a comparison between the predicted states and actual states taken from a database of body movements.

Advantageously, the covariances of state evolution noise are re-estimated a posteriori by calculating for each segment a gain index for the state evolution model from the differences between standard deviations of the sensors for actual states taken from a database of body movements and the deviations measured by said sensors.

Embodiments of the invention also disclose a method for capturing the movements of a structure including a plurality of N substantially rigid segments articulately connected with said structure, said method including a step of acquiring measurements from N accelerometers with at least one measurement axis, said accelerometers being substantially rigidly connected to said at least one segment; a step of acquiring measurements from P second sensors capable of returning one direction of a fixed reference frame, each substantially rigidly connected to a segment; a step of acquiring measurements from Q third sensors capable of returning a measurement representative of an angular velocity, each substantially rigidly connected to a segment; a step of communicating the outputs of the N accelerometers, the P second sensors and the Q third sensors to a computer processing step, said method further including a step of detecting a pseudo-static state of each of the segments of said structure, a step of calculating the pseudo-static orientation of the segments in a pseudo-static state, if at least one output of the step of detecting a pseudo-static state is false, a step replacing the outputs of a prediction function of a state observer which receives as input the outputs of the N accelerometers, the P second sensors and the Q third sensors, Q being strictly less than the number N and the number P, with the outputs of the step of calculating the pseudo-static orientation for the segments for which the detection condition at the output of the pseudo-static state detection module is true.

Advantages:

The main advantage of certain embodiments of the present invention is thus that of offering a lower cost of implementation and greater autonomy of operation. It also allows for greater adaptability to different application contexts (more or less dynamic; necessary accuracy perceived by the user, system cost, autonomy, space requirement, etc.). In fact, the method can provide an ideal á la carte system, i.e. according to the specification of the five parameters mentioned above, at least.

BRIEF DESCRIPTION OF THE DRAWINGS

Other features and advantages of the invention will become apparent from the following description referring to the following figures which illustrate examples of implementation of the method according to the present invention:

FIG. 3 shows a general flowchart of the method's processing for implementing the invention.

DETAILED DESCRIPTION

To begin with, a definition is provided of the meaning or content of a number of elements that are used in the present application.

The pseudo-static algorithms used in the present invention belong to the prior art algorithms for finding an orientation in three dimensions on the basis of knowing one or more directions of the fixed space.

A first conventional orientation calculation algorithm is TRIAD (TRI-axial Attitude Determination). See, for example, (http://en.wikipedia.org/wiki/Triad Method or Harold D. Black, *A passive system for determining the attitude of a satellite*. American Institute of Aeronautics and Astronautics Journal, 2(7): 1350-1351, July 1964). This algorithm can be used to estimate a rotation quaternion from the measurement of two reference directions.

Any other algorithm for calculating the orientation of an object in a reference frame from its position with respect to the earth's gravitational field and magnetic field vectors (or of any other uniform field) may replace the TRIAD algorithm. In particular, in the case of more than two sensors, an algorithm of the QUEST (Quaternion ESTimator) type can be used, described notably in the publication http://www.dept.aoe.vt.edu/~cdhall/courses/aoe4140/attde.pdf and, compared with TRIAD in http://www.malcolmdshuster.com/comm 1981a J TRIAD-QUEST.pdf.

A segment will be called static or pseudo-static if the error on the pseudo-static algorithm that calculates the orientation of said segment meets a threshold that is fixed (e.g. 10°). In practice, a 'staticity' detector algorithm is used based on a comparison of a threshold with the norm of the accelerometer and with the cosine of the angle between the vectors measured by the accelerometer and by the second sensor, and with the statistics of the measurements on a sliding window.

Throughout the document, the variables representing orientations are generally expressed using an angular representation. Any other form of mathematical representation of an orientation could be used as an alternative and in an equivalent manner, e.g. rotation matrices, quaternions or direction cosines.

Figure 1:
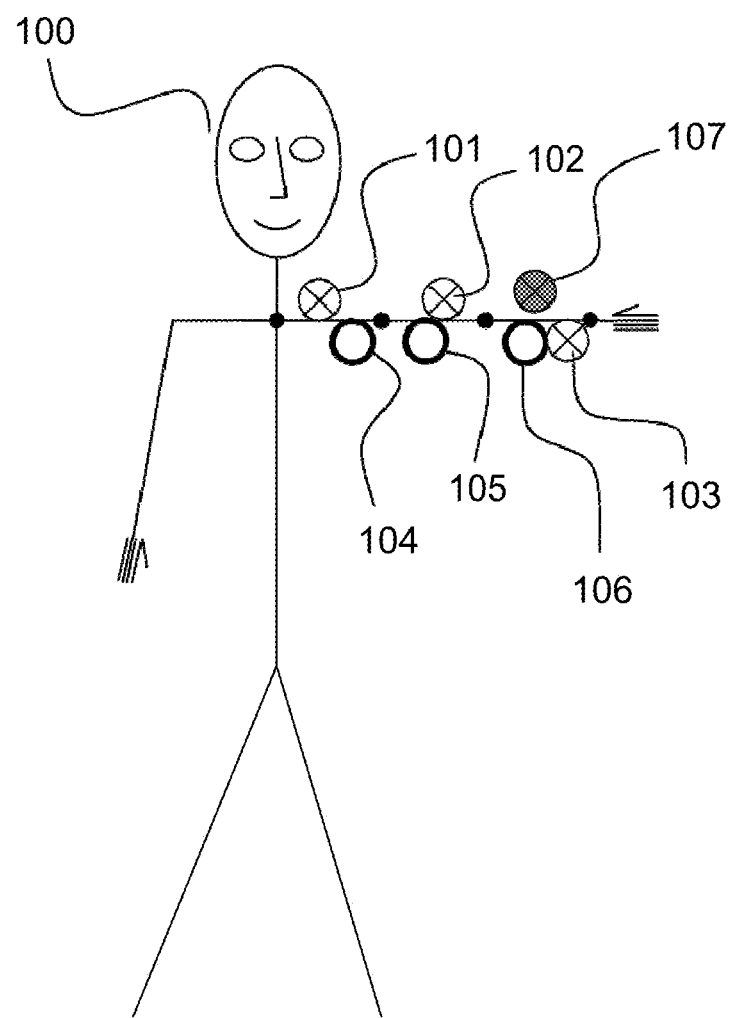
FIG. 1 illustrates an example where the structure is a human being a part of whose body is instrumented by the measurement system.

FIG. 1 illustrates an example of implementation of the invention for which three accelerometers 101, 102 and 103, three direction sensors 104, 105 and 106, and one angular velocity sensor 107, are attached to the three segments that are the shoulder of a person (to which the sensors 101 and 104 are attached), the arm of the person (to which the sensors 102 and 105 are attached), and finally the forearm of the person (to which the sensors 103, 106 and 107 are attached).

Figure 2:
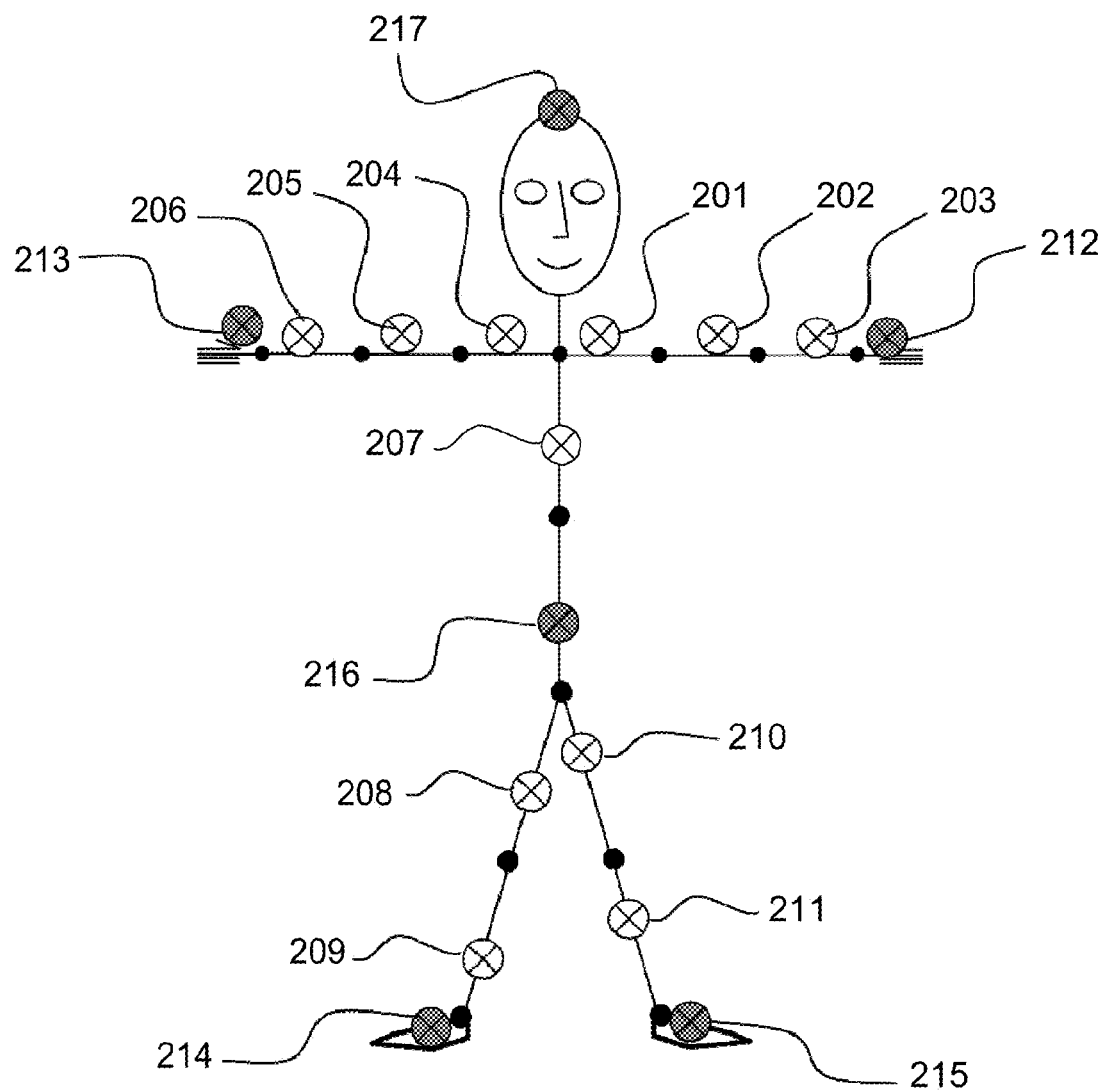
FIG. 2 illustrates an example where the structure is a human being whose entire body is instrumented by the measurement system.

FIG. 2 shows an example of implementation of the invention for which a set of 17 measuring units are distributed on the main segments of the body. This particular implementation is used for full body capture. The various measuring devices are of two types: the first comprises an accelerometer associated with a direction sensor (e.g. a magnetometer), which constitutes a first kind of measuring unit called AM (201 to 211), the second comprises a complete combination of three types of sensors (accelerometer, direction sensor and angular velocity sensor) and will be called AGM (212 to 217). The AM type units are preferably placed on the segments likely to suffer the least interference (proper acceleration and/or magnetic interference) while the AGM units will be preferably arranged on the segments likely to undergo interference of this kind. In this implementation, the segments of the body are equipped respectively as follows:

The left shoulder with the AM unit 201
The left arm with the AM unit 202
The left forearm with the AM unit 203
The left hand with the AGM unit 212
The right shoulder with the AM unit 204
The right arm with the AM unit 205
The right forearm with the AM unit 206
The right hand with the AGM unit 213
The chest with the AM unit 207
The pelvis with the AGM unit 216
The left thigh with the AM unit 210
The left tibia with the AM unit 211
The left foot with the AGM unit 215
The right thigh with the AM unit 208
The left tibia with the AM unit 209
The right foot with the AGM unit 214
The head with the AGM unit 217

For the present example of embodiment of the invention, the applicants have used AM units 201, 202, 203, 204, 205, 206, 207, 208, 209, 210, 211, which are marketed under the trade name MotionPod Version 2 and AGM units 212, 213,

214, 215, 216, 217 which each combine a triaxial accelerometer with a triaxial magnetometer and a triaxial gyroscope under the trade name MotionPod Version 3. Each of the sensors 101, 102, 103 and 104 transmits its data via a radio link to a package commonly called a master-node, this package being connected to a computer via a USB link. The package and the computer are not shown in the figure. The data can be used on the computer thanks to a programming interface marketed under the trade name Motion Development Kit (MDK). The MDK programming interface can be used either to obtain the raw and calibrated measurements of a MotionPod, or to obtain an estimate of the orientation of a MotionPod, thanks to static algorithms involving version 2 of the MotionPod. Advantageously, the present example of embodiment may consist of a development of the MDK programming interface.

This example of distributing measurement modalities over the articulated structure can be applied generally to any articulated structure including several segments organized in a tree forming a reference frame (in the example the center of mass), the tree comprising branches that themselves comprise segments including an end segment. Advantageously, the angular velocity sensors, not sensitive to magnetic interference or proper accelerations, will be placed at the ends of the segments, i.e. at the points of the branches having the longest travel. An additional angular velocity sensor, positioned, for example, at the center of mass of the tree improves the measurements. Thus, according to the invention, if R is the number of branches whereof the movements are to be captured, the number of angular velocity sensors will advantageously be equal to R+1, or optionally R. In the case of a human body whereof the movements of the four members and the head (five 'branches'), are to be captured, such as that in FIG. 2, the invention may be satisfactorily implemented with six angular velocity sensors (or even five), while 17 AM units are provided (one per segment).

Prior to using the system thus consisting of sensors 101, 102, 103 and 104 for capturing the movements of the three-segment set of shoulder-arm-forearm of the person, the change of reference frame must be evaluated between the reference frame of the solid that constitutes each segment and the reference frame of the sensor attached to said segment. Thus, the change of the reference frame between the reference frame of the shoulder and the sensor 101, the change of reference frame between the reference frame of the arm and the sensor 102, and the change of reference frame between the reference frame of the forearm and the sensor 103 must be evaluated. A fixed reference frame is also used which can be, for example, the terrestrial reference frame whereof a preferred direction will be defined by the gravity vector and/or the earth's magnetic field vector. Any method of calibration can be used for this. However, the geometric calibration method forming the subject matter of patent application no. 1252101, filed on the same day as the present application and having the same inventor and same patentees is particularly advantageous.

FIG. 3 shows a general flowchart of the method's processing for implementing an embodiment of the invention, in several of the embodiments thereof.

The figure illustrates a preferred embodiment of the invention, in which:

During steps 300, which take place at the sampling frequency of the attitude units and gyroscopes, the measurements from these sensors are provided to steps 310, 320 which may take place sequentially:

First, detection 310 of the pseudo-static state of the segments (e.g., thresholding the norm of the acceleration vector and the angle between the magnetic field vector and the acceleration) is performed;

Secondly, the calculation 320 is performed, producing the values 330 of articulation angles for the segments considered as pseudo-static in step 310, and the state vector is completed by second order derivation of the angles, and by considering the overall acceleration as zero;

If at least one of the segments is not detected in a pseudo-static state, the sensor measurements in the observer used (which may advantageously but not exclusively be a Kalman filter or an extended Kalman filter) are processed in steps 3410, 3420, whereof the processing includes:

A step 3410 of calculating evolution/prediction during which the segments in a pseudo-static state are processed in such a way that the predicted angles are equal to the static angles at the output of step 320, the evolution covariance being modified as described above, the segments in a dynamic state being processed by prediction of the angles under the assumption of constancy of angular acceleration; at the output of these sub-steps, a prediction is made of the overall acceleration and the covariance matrix is modified according to the measurement statistics, as explained above;

A step of correcting 3420 the outputs of the evolution step 3410 by reinjecting the prediction/measurement differences modified by the gain of the filter according to the method conventionally applied in a Kalman filter;

At the output of steps 320 and 340, the values 350 are retrieved of the estimated states, either of the branch 320, if all the segments have been detected in a pseudo-static state, or of the branch 340, if at least one segment has been detected in a dynamic state.

In FIG. 3, the numerical references equally designate the steps of the method of the invention and the system modules capable of being implemented.

Once the geometric calibration of the sensor port is assured with respect to the articulated structure, the system is ready for effectively capturing the movements of the person. For this, the orientation angles of the segments must be constantly evaluated with the aid of the distributed measurement device.

A first method of local resolution used in the prior art consists in independently determining the orientation angles of each of the segments with the aid of an angle sensor (e.g. an AM or AGM unit). But this method is not very effective, since it cannot be used to take advantage of the reduced number of degrees of freedom made possible by the geometric constraints linking the articulated members together. More precisely, the local method cannot take into account the mechanical link (law of composition of movements) between the segments that result in the accelerometer measurement model for all segments.

In the local method using AM units, pseudo-static assumptions are made: the proper acceleration of the sensors is considered negligible. Unfortunately, this assumption very quickly becomes problematic in the context of capturing the movements of a whole body, during which a simple arm movement can create accelerations that invalidate the pseudo-static assumption.

In the local method using AGM units, the pseudo-static assumptions are lifted; however, the measurement system appears too expensive (price, energy, use).

Furthermore, the previous two solutions can lead to results that do not respect the mechanical constraints or links.

This is why various embodiments of the present invention provide a method of original global resolution for simultaneously evaluating at lower cost all the orientation angles of the segments, by estimating their first and second derivatives for expressing the inter-segment mechanical links. Thus, according to embodiments of the invention, the problem to be addressed is written as the inverse of the following direct problem:

Measurement=function(State)

Where:

Measurement=[Measurement Accelerometer,Measurement Magnetometer, Measurement Gyroscope]

(notation in which Magnetometer can be replaced by 'Second direction sensor' and Gyroscope by 'angular velocity sensor')
function: a measurement function
state: all the variables expressing the measurements, including the angles, and their first and second derivatives with respect to time, and the frame acceleration of the whole articulated structure. Hereafter this state is denoted by x and $\dot{x}$ its derivative with respect to time.

For a description of the various combinations of sensors, the choice of their number and their positioning, refer to the comments above relating to FIGS. 1 and 2.

For expressing the link between the various angles and their derivatives, embodiments of the present invention propose to model the problem in a state system including an evolution function of the system, denoted as evolution in the equations that follow. Thus, according to embodiments of the proposed invention, the problem is expressed as follows:

$$\begin{cases} \text{Measurement} = \text{function}(x) \\ \dot{x} = \text{evolution}(x) \end{cases}$$

Furthermore, in order to address this problem whatever the type of movement that the articulated structure bearing the measurement system performs, (fast or slow movements), embodiment methods of the invention use a hybrid resolution model of the problem. This resolution model according to the invention is hybrid in the sense that it implements an observer (e.g. a Kalman filter, an iterative inversion method, error minimization between observed and model data) comprising a pseudo-static operating mode and a dynamic operating mode, the estimates of the latter mode are initialized with the aid of those of the former (which amounts to performing a resetting of the filter on an initial state considered more stable) for calculating angles when the pseudo-staticity condition is fulfilled for a given sensor This condition is verified thanks to a function for detecting pseudo-immobility of the sensors.

In the dynamic mode, estimation is initialized from the previous data according to the chosen evolution. In the case where the observer is a Kalman filter, this initialization is the first step called evolution and the covariances of said filter are set empirically.

The pseudo-static mode is more specific. It receives as input the pseudo-static angles on one or more segments when said segments are subjected to a pseudo-static movement, i.e. a slow and regular movement with a proper acceleration of less than 0.1 G. In this mode, estimation is more reliable since the number of degrees of freedom is less than in the dynamic mode. Indeed the pseudo-static algorithms are stable: for a given measurement configuration, there is only one solution. In the case of the Kalman filter, the covariance values are set empirically. In addition, the invention provides a function for deactivating the Kalman filter if all the segments follow a pseudo-static movement, and for activating the pseudo-static algorithms for all the segments.

An extended Kalman filter can be used for implementing the invention. Such a filter is known as an Extended Kalman Filter or EKF. But other types of observer may be used without any difficulty and without departing from the scope of the present invention. A Kalman filter requires the setting of various parameters, such as the covariances. Even if the basic settings of the filter may be governed by more or less empirical laws, its fine tuning can be carried out only through practical trials.

For the rest of the description, we shall use a Kalman filter as an observer. Several methods can be used to define a prediction function for the filter, this function corresponding to the evolution function. It must first predict the angles and their derivatives, and secondly the overall acceleration.

Regarding the prediction of the angles and their derivatives, in the context of the implementation of the present invention, the kinematic assumption may, for example, be made that the second derivatives are equal to constants (zero jerk) and these constants integrated. Indeed, given the high sampling rate, of the order of 200 Hertz in the case of the MotionPod2s (AM units), an order of magnitude higher than the frequencies of human gestures (of the order of ten or so hertz for the most dynamic movements), the accelerations can be estimated as constant in a first approximation without harm. Thus, the kinematic model is defined from the vector of the state variables which are the three Cardan angles (yaw, pitch and roll), which set the parameters of the articular rotations and their two successive derivatives:

$$x = \begin{bmatrix} \text{yaw}_1, \dfrac{d\text{yaw}_1}{dt}, \dfrac{d^2\text{yaw}_1}{dt^2}, \text{pitch}_1, \dfrac{d\text{pitch}_1}{dt}, \dfrac{d^2\text{pitch}_1}{dt^2}, \text{roll}_1, \dfrac{d\text{roll}_1}{dt}, \dfrac{d^2\text{roll}_1}{dt^2}, \\ \ldots \\ \text{yaw}_s, \dfrac{d\text{yaw}_s}{dt}, \dfrac{d^2\text{yaw}_s}{dt^2}, \text{pitch}_s, \dfrac{d\text{pitch}_s}{dt}, \dfrac{d^2\text{pitch}_s}{dt^2}, \text{roll}_s, \dfrac{d\text{roll}_s}{dt}, \dfrac{d^2\text{roll}_s}{dt^2}, \\ \text{Acc\_overall}_x, \text{Acc\_overall}_y, \text{Acc\_overall}_z \end{bmatrix}$$

It will be noted that for a complete articulated structure comprising S=22 segments, considering that all the articulations have three degrees of freedom, the dimension of the state vector is 22*9+3=201.

These three angles being governed by the same equations, they will be equally denoted by θ, together with their first and second derivatives which will be equally respectively denoted by $\dot{\theta}$ and $\ddot{\theta}$ in the rest of this description. The frame acceleration of the whole body will be denoted by Acc_overall or sometimes Acc for simplification. Thus, under the assumption of constancy of the angular second derivatives, and of the frame acceleration of the whole body, we have:

$$\begin{cases} \dddot{\theta} = cst_1 \\ \dot{Acc} = cst_2 \end{cases}$$

With the state model $x=[\theta, \dot{\theta}, \ddot{\theta}, Acc_x, Acc_y, Acc_z]$ where the last three state variables are the coordinates of the overall acceleration in a terrestrial reference frame (X, Y, Z), a continuous evolution function can thus be defined by:

$$\dot{x} = \begin{bmatrix} 0 & 1 & 0 & 0 & 0 & 0 \\ 0 & 0 & 1 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \end{bmatrix} * x + \begin{bmatrix} v_\theta \\ v_{\dot{\theta}} \\ v_{\ddot{\theta}} \\ v_{Acc\_x} \\ v_{Acc\_y} \\ v_{Acc\_z} \end{bmatrix} \quad \text{eq. 1}$$

with $v_i$ noise where the terms $v_\theta$, $v_{\dot{\theta}}$, $v_{\ddot{\theta}}$, $v_{Acc\_x}$, $v_{Acc\_y}$, and $v_{Acc\_z}$, are noise terms.

In this continuous formalism, the evolution function connects the state with its derivative, or even with its successive derivatives. It should be noted that this continuous state model is easily transposable to a larger number of degrees of freedom. The standard deviation values are chosen relatively large for $v_{\ddot{\theta}}$, $v_{Acc\_x}$, $v_{Acc\_y}$, and $v_{Acc\_z}$, since the assumption of the constancy of angular acceleration and overall acceleration is strong and not necessarily verified. On the other hand, $v_\theta$, $v_{\dot{\theta}}$, are correlated with $v_{\ddot{\theta}}$ and the model used is therefore rather.

$$\dot{x} = \begin{bmatrix} 0 & 1 & 0 & 0 & 0 & 0 \\ 0 & 0 & 1 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \end{bmatrix} * \left( x + \begin{bmatrix} 0 \\ 0 \\ v_{\ddot{\theta}} \\ 0 \\ 0 \\ 0 \end{bmatrix} \right) + \begin{bmatrix} v_\theta \\ v_{\dot{\theta}} \\ v_{\ddot{\theta}} \\ v_{Acc\_x} \\ v_{Acc\_y} \\ v_{Acc\_z} \end{bmatrix} \quad \text{eq. 2}$$

Indeed, the error on the assumption $\ddot{\theta}$=constant is integrated and transmitted to the angular derivatives and to the angles. This model can be discretized, giving the following evolution function:

$$x_{t+1} = \exp\left( \begin{bmatrix} 0 & 1 & 0 & 0 & 0 & 0 \\ 0 & 0 & 1 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \end{bmatrix} * Te \right) * \left( x_t + \begin{bmatrix} 0 \\ 0 \\ v_{\ddot{\theta}} \\ 0 \\ 0 \\ 0 \end{bmatrix} \right) + Te * \begin{bmatrix} v_\theta \\ v_{\dot{\theta}} \\ v_{\ddot{\theta}} \\ v_{Acc\_x} \\ v_{Acc\_y} \\ v_{Acc\_z} \end{bmatrix} \quad \text{eq. 3}$$

where Te designates the period elapsing between an instant t and an instant t+1, i.e. the sampling frequency. In this discrete formalism, the evolution function connects the state at instant t to the state at instant t+1.

That is:

$$x_{t+1} = \begin{bmatrix} 1 & Te & \frac{Te^2}{2} & 0 & 0 & 0 \\ 0 & 1 & Te & 0 & 0 & 0 \\ 0 & 0 & 1 & 0 & 0 & 0 \\ 0 & 0 & 0 & 1 & 0 & 0 \\ 0 & 0 & 0 & 0 & 1 & 0 \\ 0 & 0 & 0 & 0 & 0 & 1 \end{bmatrix} * \left( x_t + \begin{bmatrix} 0 \\ 0 \\ v_{\ddot{\theta}} \\ 0 \\ 0 \\ 0 \end{bmatrix} \right) + Te * \begin{bmatrix} v_\theta \\ v_{\dot{\theta}} \\ v_{\ddot{\theta}} \\ v_{Acc\_x} \\ v_{Acc\_y} \\ v_{Acc\_z} \end{bmatrix} \quad \text{eq. 4}$$

Under the assumption that the movement does not comprise a fixed point, the prediction of the overall acceleration corresponds to the acceleration of the first segment in the terrestrial reference system, expressed in the terrestrial reference frame that has been chosen. The first segment means the segment from which the mathematical model of the skeleton is defined, the other segments being defined with respect to this first segment. For predicting this overall acceleration, the invention proposes the use of the sensor measurements and the angles which have been predicted by the method previously described (eq. 4).

For this, the following measurement function can be used for each accelerometer:

$$\text{Mes\_Acc} = {}^{Sensor}R_{Earth} * \left( G0 - \left( \frac{\partial^2 {}^{Earth}T_{Sensor}}{\partial t^2} + \text{Acc\_overall} \right) \right) \quad \text{eq. 5}$$

Where Mes_Acc designates the acceleration measured by the accelerometer, ${}^{Sensor}R_{Earth}$ designates the matrix of rotation of the terrestrial reference frame toward a reference frame associated with this accelerometer, ${}^{Earth}T_{Sensor}$ designates the translation vector from the reference frame associated with the accelerometer to the terrestrial reference frame.

Hence:

$$\begin{aligned} Acc = \text{Acc\_overall} &= -{}^{Earth}R_{Sensor} * \text{Mes\_Acc} + G0 - \frac{\partial^2 {}^{Earth}T_{Sensor}}{\partial t^2} \\ &= -{}^{Earth}R_{Sensor} * \left( \text{Mes\_Acc} + {}^{Sensor}R_{Earth} * \left( G0 - \frac{\partial^2 {}^{Earth}T_{Sensor}}{\partial t^2} \right) \right) \end{aligned} \quad \text{eq. 6}$$

Where ${}^{Earth}R_{Sensor}$ denotes the matrix of rotation of the reference frame associated with the accelerometer toward the terrestrial reference frame.

The overall acceleration can then be estimated by taking Mes_Acc=Mes_Acc_actual. Another possibility consists in using the simulated measurement for an overall acceleration of zero Mes_Acc$_{Acc\_overall=0}$:

$$\text{Mes\_Acc}_{Acc\_overall=0} = {}^{Sensor}R_{Earth} * \left( G0 - \left( \frac{\partial^2 {}^{Earth}T_{Sensor}}{\partial t^2} \right) \right) \quad \text{eq. 7}$$

Where the matrix ${}^{Sensor}R_{Earth}$ is defined for angles=angles_predicted and Acc=0. This means, for the angles predicted thanks to the evolution function, changing from an angular formalism to a matrix formalism.

This vector of theoretical measurements Mes_Acc$_{Acc\_overall=0}$ is deduced by calculating the theoretical measurement of the accelerometer from the assumption stated above that the overall acceleration is zero (the base point for constructing the skeleton has a zero acceleration).

By replacing the term $${}^{Sensor}R_{Earth} * \left( G0 - \frac{\partial^2 {}^{Earth}T_{Sensor}}{\partial t^2} \right)$$

by Mes_Acc$_{Acc\_overall=0}$:

$$\text{Acc\_overall} = {}^{Earth}R_{Sensor} * (\text{Mes\_Acc\_actual} - \text{Mes\_Acc}_{Acc\_overall=0}) \quad \text{eq. 8}$$

This estimation is performed on each sensor, then these estimates are averaged to reduce the estimation error. Which then gives:

$$\text{Acc\_overall\_predicted} = \underset{sensor}{\text{mean}}(\text{Acc\_overall}_{sensor}) \quad \text{eq. 9}$$

This method offers the advantage of forcing the coupling of the sensors beyond the joint information already carried by the articulated chain modeling of segments.

In order to test the pseudo-static assumption, an observer is created which monitors the level of one or more of the following variables:
  the norm of the accelerometer, which should be close to 1 G if there is immobility,
  the angle between the measurement of the earth's magnetic field and the measurement of the acceleration field,
  the standard deviation of certain measurements of the sensors in a sliding window. For example, the norm of the accelerometer measurements.
  etc.

Then the decision thresholds just need to be set. The pseudo-static assumption is considered verified if the values are below their respective thresholds. Naturally, the thresholds on the standard deviations depend on the sensor noise. The size of the sliding window and the thresholds are set empirically.

For example, a window of 10 samples at 200 Hz may be used, and threshold values equal to 0.0455 for the difference from the accelerometer norm at 1 (gravity) and 0.0333 for the difference of the cosine from its reference value, 0.0526 for the standard deviation on the magnetometer, and 0.0467 for the norm of the standard deviation on the accelerometer.

As stated earlier, at the output of the pseudo-staticity detection, the pseudo-static angles are injected into the Kalman filter replacing the angles predicted by the first step of the filter.

In the movement dynamics of a whole body over a sufficiently wide time range, an average period of return to immobility is found of the order of 30 to 60 s.

As mentioned previously, the use of Kalman filters presupposes the estimation of measurement noise and evolution covariances. For setting these covariances within the context of the implementation of the present invention, advantageously two methods of setting will be implemented jointly: a priori setting and a posteriori setting.

With regard to a priori setting, the covariance of measurement noise is quite simple. Indeed, for accelerometers as for magnetometers, this noise can advantageously be modeled as a bias-free additive noise, i.e.:

$$\text{Measurement} = \text{Measurement}_{perfect} + \text{noise} \quad \text{eq. 10}$$

It therefore suffices to make a sufficiently long static measurement, of the order of a minute, and to calculate the covariance of the measurement:

$$\text{Covariance} = \frac{((\text{Measurement}) * (\text{Measurement})^T)}{\text{Measurement Number} - 1} - ((\text{mean}(\text{Measurement})) * (\text{mean}(\text{Measurement}))^T) \quad \text{eq. 11}$$

Where mean designates the arithmetic mean.

Still with regard to a priori setting, the modeling of evolution noise is more complex. It is considered as an additive noise, denoted by noise$_{post-evolution}$, which corresponds to digitization noise (which should be low), and a model noise, denoted by noise$_{pre-evolution}$, which is dominant since it actually corresponds to the error made by considering the assumption $\ddot{\theta}$ constant.

For evaluating evolution covariances, examples of movements have been advantageously selected in the movements database in the Bio Vision Hierarchy (BVH) format of the Motion Capture Laboratory of the Advanced Computing Center of Art and Design of Columbus (Ohio, USA), the goal being to conduct a series of tests covering all the intended cases of use. The evolution function with the actual angles at instant k is then applied on each of the tests and the result is compared with the actual angles at the instant k+1. Giving:

$$\text{diff}(x) = x_{actual} - x_{predicted}$$

$$\text{covariance}_{evolution} = \frac{(\text{diff}(x) * \text{diff}(x)^T)}{\text{number\_of\_samples} - 1} - (\text{mean}(\text{diff}(x)) * \text{mean}(\text{diff}(x))^T) \quad \text{eq. 12}$$

Then:

$$\text{diff}(\dot{\theta}) = \dot{\theta}\text{ actual} - \dot{\theta}\text{ predicted} - Te * \text{diff}(\ddot{\theta})$$

$$\text{Covariance}_{post\_evo.\dot{\theta}} = \frac{(\text{diff}(\dot{\theta}) * \text{diff}(\dot{\theta})^T)}{\text{Number of samples} - 1} - (\text{mean}(\text{diff}(\dot{\theta})) * \text{mean}(\text{diff}(\dot{\theta}))^T) \quad \text{eq. 13}$$

Even if these noise variables are deterministic, an optimization of the corresponding parameters can improve the convergence of the algorithms. However, an effort must be made, by selecting the movements forming the subject of the tests, to remain generic and not to choose settings specific to a certain type of movement; except precisely in the case of a specific use. Typically, if very high dynamic movements have to be studied, the evolution covariance should, on the assumption that e is equal to a constant, be taken large since the assumption will be little respected. Conversely, in a low dynamic movement, a low covariance should be preferred. However, despite all the a prioris that can be made on the settings, it may be useful to seek to optimize the settings on a large number of examples, in order to maximize the angular precision of the estimates. Typically the number of examples may be of the order of twenty examples of gestures, with a duration of 60 seconds. It should be recalled that the size of the state vector is of the order of 201 for a complete articulated chain, which leads to a covariance matrix of size 201×201.

Dynamic setting consists in observing the measurements for anticipating the dynamics of the movement and thus of the state variables. The covariance matrix of the model can then be modified dynamically according to this observer. In concrete terms, an std function will be used to calculate the standard deviation of the accelerometer, magnetometer, and where applicable gyroscope, measurements, if they are available for each segment, then a function will be used, hereafter denoted by function, for calculating a dynamism index or gain $gain_{segment}$ for each segment:

$$gain_{segment} = function(std(MesAcc_{[t-9,i]}), \quad \text{eq. 14}$$
$$std(MesMag_{[t-9,i]}), std(MesGyro_{[t-9,i]}))$$

Finally, the evolution covariance matrix Q is multiplied by this gain:

$$Q = gain\_segment * Q(segment)$$

$Q(segment)$ being the part of $Q$ corresponding to a segment    eq. 15

For obtaining an optimum resolution, the function function, must be adapted, as for example:

$$function(sAcc, sMag, sGyro) = gain * mean\left(\left(\frac{sAcc - oAcc}{rAcc}\right)^{eAcc}, \quad \text{eq. 16}$$
$$\left(\frac{sMag - oMag}{rMag}\right)^{eMag}, \left(\frac{sGyro - oGyro}{rGyro}\right)^{eGyro}\right)$$

Where:
gain: overall gain
sAcc, sMag, sGyro: standard deviations on 10 samples (accelerometer, magnetometer and gyroscope respectively)
oAcc, rAcc, eAcc: coefficients on the accelerometer (offset, ratio and exponent respectively)
oMag, rMag, eMag: coefficients on the magnetometer (offset, ratio and exponent respectively)
oGyro, rGyro, eGyro: coefficients on the gyroscope (offset, ratio and exponent respectively)

The values of the various coefficients used to define function are advantageously set by optimization on all the test files in BVH format. For this, the acceptable value ranges are scanned by performing a comprehensive resolution on all the test files. This identifies the optimum values. Thus, the following results were obtained by the applicants:

$$\begin{cases} oAcc = 1208.969 \\ rAcc = 0.046 \\ eAcc = 1.000 \\ oMag = 130.662 \\ rMag = 0.034 \\ eMag = 1.000 \\ oGyro = 1089.051 \\ rGyro = 0.013 \\ eGyro = 1.000 \\ gain = 0.085 \end{cases}$$

When looking at the order of magnitude of the various states on any movement, it is seen that the angular derivative has an order of magnitude higher than the angle and that the second derivative has a still higher order of magnitude. Accordingly, in order to reduce the digital calculation errors, it may be advantageous to normalize the corresponding states by putting:

$$\begin{cases} \dot{\theta} \text{ modified} = \frac{1}{10} * \dot{\theta} \\ \ddot{\theta} \text{ modified} = \frac{1}{100} * \ddot{\theta} \end{cases} \quad \text{eq. 17}$$

It is then necessary to correct the measurement and evolution functions to take into account this normalization. The correction amounts to simply multiplying the states by 10 and 100 before performing the calculations, as well as the columns of the Jacobian matrix associated with the states concerned. It is also necessary to modify the covariances associated with the states, dividing by the same value as the associated state.

The various equations presented above are not modified by the number of state variables.

Variations can be applied to the order of the steps and to the criteria for some of them, notably the pseudo-static state detection criterion and the steps of the Kalman filter, without departing from the general scope of the present invention. The observer is not necessarily a Kalman filter.

These steps of the embodiment method are implemented in software, certain parts of the software being able to be embedded in the sensors, others being able to be installed on a microcontroller, a microprocessor or a microcomputer connected to the sensor system. These processing capabilities are ordinary circuits, connected and configured for performing the processing described above.

The examples described above are given by way of illustration of embodiments of the invention. They do not limit in any way the scope of the invention which is defined by the following claims.

The invention claimed is:
1. A system for capturing movements of a structure including at least N substantially rigid segments articulately connected with said structure, said system including:
  a set of N accelerometers with at least one measurement axis, each of said N accelerometers being substantially rigidly connected to one of said N segments,
  a set of P second sensors capable of returning one direction of a fixed reference frame, each substantially rigidly connected to a segment, a set of Q third sensors capable of returning a measurement representative of an angular velocity, each substantially rigidly connected to a segment,
a module for communicating the outputs of the N accelerometers, P second sensors and Q third sensors with a computer processing module;
said processing module including a state observer,
said system further including:
   a pseudo-static state detection module for detecting a pseudo-static state of each of the segments of said structure,
   a pseudo-static orientation calculation module for calculating a pseudo-static orientation of the segments in a pseudo-static state,
   a state observer module configured for replacing outputs of a prediction function of the state observer with outputs of the pseudo-static orientation calculation module for the segments for which a detection condition at the output of the pseudo-static state detection module condition is true
wherein the number Q is less than the number N and the number P.

2. The system for capturing movements as claimed in claim 1, wherein R is equal to a number of branches of the structure whereof the movement is captured, the number Q being less than or equal to R+1.

3. The system for capturing movements as claimed in claim 1, wherein the second sensors are magnetometers.

4. The system for capturing movements as claimed in claim 3, wherein the third sensors are gyroscopes.

5. The system for capturing movements as claimed in claim 4, wherein the observer is a Kalman filter.

6. The system for capturing movements as claimed in claim 5, wherein the modules thereof are configured by state evolution models of the form:

$$\begin{cases} \text{Measurement} = \text{function}(x) \\ \dot{x} = \text{evolution}(x) \end{cases}$$

where:
   x designates a state vector of the body;
   function designates a characteristic measurement function of the accelerometers, magnetometers and gyroscopes;
   Measurement=[Measurement Accelerometer, Measurement Magnetometer, Measurement Gyroscope] designates a measurement vector provided by the accelerometers, magnetometers and gyroscopes;
   $\dot{x}$ designates the first derivative of x with respect to time; and
   evolution designates an evolution function of the body state.

7. The system for capturing movements as claimed in claim 6, wherein the state vector x is of the form $x=[\theta, \dot{\theta}, \ddot{\theta}, Acc_x, Acc_y, Acc_z]$ where $\theta$, $\dot{\theta}$ and $\ddot{\theta}$ respectively designate an orientation angle of the segments, its first derivative and its second derivative with respect to time, and where $Acc_x$, $Acc_y$ and $Acc_z$ designate components of a frame acceleration Acc of the whole of the body in a terrestrial reference frame (X, Y, Z).

8. The system for capturing movements as claimed in claim 6, wherein the state evolution model of the Kalman filter uses said pseudo-static angles for the segments detected in a pseudo-static state and the state evolution model of the Kalman filter for the segments detected in a dynamic state.

9. The system for capturing movements as claimed in claim 8, wherein the state evolution model of the Kalman filter uses an assumption of constancy of accelerations of the articulation angles.

10. The system for capturing movements as claimed in claim 6, wherein the state vector is estimated from pseudo-static angles at the output of the pseudo-static orientation calculation module, if all the segments are detected in a pseudo-static state and is estimated by the Kalman filter, if at least one segment is detected in a dynamic state.

11. The system for capturing movements as claimed in claim 6, wherein a criterion of pseudo-staticity is fulfilled by a segment when at least one of the values provided by at least one of the elements of the group including an attitude unit or a gyroscope which is rigidly connected thereto provides at least one measurement chosen from the norm of an acceleration vector and an angle between said acceleration vector and a magnetic field vector which is less than a predetermined threshold value.

12. The system for capturing movements as claimed in claim 6, wherein the state evolution model of the Kalman filter predicts the angle $\theta$, its first derivative $\dot{\theta}$ and its second derivative $\ddot{\theta}$ via the function defined by:

$$\dot{x} = \begin{bmatrix} 0 & 0 & 0 & 0 & 0 & 0 \\ 1 & 0 & 0 & 0 & 0 & 0 \\ 0 & 1 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \end{bmatrix} * \left(x + \begin{bmatrix} 0 \\ 0 \\ 0 \\ 0 \\ 0 \\ 0 \end{bmatrix}\right) + \begin{bmatrix} v_\theta \\ v_{\dot{\theta}} \\ 0 \\ v_{Acc\_x} \\ v_{Acc\_y} \\ v_{Acc\_z} \end{bmatrix}$$

where $v_\theta$, $v_{\dot{\theta}}$, $v_{\ddot{\theta}}$, $v_{Acc\_x}$, $v_{Acc\_y}$ and $v_{Acc\_z}$ and are noise terms on the measurement of $\theta$, $\dot{\theta}$, $\ddot{\theta}$, $Acc_x$, $Acc_y$ and $Acc_z$ respectively.

13. The system for capturing movements as claimed in claim 6, wherein the state evolution model of the Kalman filter predicts the frame acceleration Acc as a mean of frame accelerations Acc_overall calculated for each accelerometer from a measurement vector Mes_Acc_actual actually provided by said accelerometer, the frame acceleration Acc_overall being calculated for each accelerometer by:

Acc_overall$=-^{Earth}R_{Sensor}*$(Mes_Acc_actual$-$Mes_Acc$_{Acc\_overall=0}$)

Where $^{Earth}R_{Sensor}$ designates a matrix of rotation of a reference frame associated with said accelerometer toward the terrestrial reference frame, and Mes_ACC$_{Acc\_overall=0}$ designates a theoretical measurement vector calculated by assuming that the overall acceleration is zero.

14. The system for capturing movements as claimed in claim 6, wherein the accelerometer measurement model of the Kalman filter is given by:

$$\text{Mes\_Acc} = {}^{Sensor}R_{Earth} * \left( G0 - \left( \frac{\partial^2 \, {}^{Earth}T_{Sensor}}{\partial t^2} + \text{Acc\_overall} \right) \right)$$

where Mes_Acc designates a vector of measurements taken by said accelerometer, $^{Earth}R_{Sensor}$ designates a matrix of rotation of a reference frame associated with the accelerometer toward the terrestrial reference frame, G0 is the earth's gravitational field measured from an initial position in the reference frame associated with the accelerometer and $^{Earth}T_{Sensor}$ is a translation vector from the terrestrial reference frame to the reference frame associated with the accelerometer.

15. The system for capturing movements as claimed in claim 6, wherein covariances of the measurement and state evolution noise are estimated both a priori and a posteriori.

16. The system for capturing movements as claimed in claim 6, wherein covariances of state evolution noise are estimated a priori from a comparison between predicted states and actual states taken from a database of body movements.

17. The system for capturing movements as claimed in claim 6, wherein covariances of state evolution noise are re-estimated a posteriori by calculating for each segment a gain index for the state evolution model from differences between standard deviations of the sensors for actual states taken from a database of body movements and deviations measured by said sensors.

18. A method for capturing movements of a structure including at least N substantially rigid segments articulately connected with said structure, said method including:
  a step of acquiring measurements from N accelerometers with at least one measurement axis, said accelerometers being substantially rigidly connected to said segments,
  a step of acquiring measurements from P second sensors configured to return a direction of a fixed reference frame, each substantially rigidly connected to a segment,
  a step of acquiring measurements from Q third sensors configured to return a measurement representative of an angular velocity, each substantially rigidly connected to a segment, and
  a step of communicating outputs of the N accelerometers, the P second sensors and the Q third sensors to a computer processing step comprising:
  a step of detecting a pseudo-static state of each of the segments of said structure,
  a step of calculating a pseudo-static orientation of the segments in a pseudo-static state, and
  if at least one output of the step of detecting a pseudo-static condition is false, a step of replacing outputs of a prediction function of a state observer which receives as input the outputs of the N accelerometers, the P second sensors and the Q third sensors, Q being less than the number N and the number P, with the outputs of the step of calculating the pseudo-static orientation for the segments for which the detection condition at an output of the pseudo-static state detection module is true.

* * * * *